US007816546B2

(12) United States Patent
Tuba et al.

(10) Patent No.: US 7,816,546 B2
(45) Date of Patent: Oct. 19, 2010

(54) PROCESS FOR THE SYNTHESIS OF HIGH PURITY D-(17α)-13-ETHYL-17-HYDROXY-18, 19-DINO-RPREGN-4-ENE-20-YN-3-ONE-OXIME

(75) Inventors: Zoltán Tuba, Budapest (HU); Sándor Mahó, Budapest (HU); János Kiss, Budapest (HU); Endréné Magyari, Albertirsa II (HU); László Terdy, Budapest (HU)

(73) Assignee: Richter Gedeon Vegyeszeti Gyar Rt., Budapest (HU)

( * ) Notice: Subject to any disclaimer, the term of this patent is extended or adjusted under 35 U.S.C. 154(b) by 1659 days.

(21) Appl. No.: 10/879,708

(22) Filed: Jun. 30, 2004

(65) Prior Publication Data
US 2005/0032763 A1 Feb. 10, 2005

(30) Foreign Application Priority Data
Jun. 30, 2003 (HU) .................................... 0301981
Jun. 30, 2003 (HU) .................................... 0301982

(51) Int. Cl.
*C07J 41/00* (2006.01)
(52) U.S. Cl. ..................................................... 552/520
(58) Field of Classification Search .................. 552/520
See application file for complete search history.

(56) References Cited

U.S. PATENT DOCUMENTS

| 2,774,777 | A | | 12/1956 | Djerassi et al. |
| 3,012,046 | A | * | 12/1961 | Schroeter et al. ............. 552/520 |
| 3,299,107 | A | * | 1/1967 | Mazur ......................... 552/520 |
| 3,437,674 | A | | 4/1969 | Shroff |
| 3,532,689 | A | | 10/1970 | Shroff |
| 3,545,397 | A | | 12/1970 | Andrews |
| 3,629,415 | A | | 12/1971 | Shroff |
| 3,761,496 | A | | 9/1973 | Tuba et al. |
| 3,780,073 | A | | 12/1973 | Shroff |
| 3,912,768 | A | | 10/1975 | Gardi et al. |
| RE28,690 | E | | 1/1976 | Lehmann et al. |
| 3,941,840 | A | * | 3/1976 | Rotaru ......................... 564/259 |
| 3,959,322 | A | | 5/1976 | Hughes et al. |
| 3,975,412 | A | | 8/1976 | Stein |
| 4,012,496 | A | | 3/1977 | Schöpflin et al. |
| 4,027,019 | A | * | 5/1977 | Shroff ......................... 514/182 |
| 4,144,254 | A | | 3/1979 | Imai et al. |
| 4,186,128 | A | | 1/1980 | Warnant et al. |
| 4,292,965 | A | | 10/1981 | Nash et al. |
| 4,368,160 | A | | 1/1983 | Boór nee Mezei et al. |
| 4,871,543 | A | | 10/1989 | Lindskog et al. |
| 4,906,169 | A | | 3/1990 | Chien et al. |
| 4,906,463 | A | | 3/1990 | Cleary et al. |
| 4,973,468 | A | | 11/1990 | Chiang et al. |
| 5,006,342 | A | | 4/1991 | Cleary et al. |
| 5,059,426 | A | | 10/1991 | Chiang et al. |
| 5,188,835 | A | | 2/1993 | Lindskog et al. |
| 5,252,334 | A | | 10/1993 | Chiang et al. |
| 5,422,119 | A | | 6/1995 | Casper |
| 5,474,783 | A | | 12/1995 | Miranda et al. |
| 5,656,286 | A | | 8/1997 | Miranda et al. |
| 5,876,746 | A | | 3/1999 | Jona et al. |
| 5,958,446 | A | | 9/1999 | Miranda et al. |
| 5,972,377 | A | | 10/1999 | Jona et al. |
| 6,024,976 | A | | 2/2000 | Miranda et al. |
| 6,071,531 | A | | 6/2000 | Jona et al. |
| 2003/0219471 | A1 | | 11/2003 | Caubel et al. |
| 2003/0225047 | A1 | | 12/2003 | Caubel et al. |
| 2003/0225048 | A1 | | 12/2003 | Caubel et al. |
| 2003/0229057 | A1 | | 12/2003 | Caubel et al. |
| 2004/0043171 | A1 | | 3/2004 | Audett |
| 2004/0266741 | A1 | | 12/2004 | Tombari et al. |
| 2006/0035872 | A1 | | 2/2006 | Villa et al. |
| 2007/0149812 | A1 | | 6/2007 | Farnesi et al. |

FOREIGN PATENT DOCUMENTS

| AT | 348 151 B | 2/1979 |
| CA | 1122592 | 4/1982 |
| CH | 494 218 | 7/1970 |
| DE | 136502 | 7/1979 |

(Continued)

OTHER PUBLICATIONS

Sisenwine, Samuel F. et al: "The conversion of d-norgestrel-3-oxime-17-acetate to d-norgestrel in female rhesus monkeys" Contraception, vol. 15(1), 25-37, 1977.*

Houben-Weyl, "Methoden der Organischen Chemie," Müller, E., ed., Georg Thieme Verlag, Stuttgart, Germany p. 291 (1968), to the extent discussed by applicant.

Rufer, C., et al., "Totalsynthese von optisch aktiven 13-Äthyl-gonan-Derivaten," *Liebigs Annalen der Chemie* 702:141-148, (Verlag Chemie, Germany) (1967), Abstract only.

Sisenwine, S.F., et al., "The Conversion of *d*-Norgestrel-3-Oxime-17-Acetate to *d*-Norgestel in Female Rhesus Monkeys," *Contraception* 15:25-37, (Geron-X, Inc., Los Altos, CA) (1977).

Derwent World Patent Index, Dialog File 351, English Language Abstract for Swiss Patent No. CH 494 218 (Document AM2), Accession No. 532761, 2005.

(Continued)

*Primary Examiner*—Barbara P Badio
(74) *Attorney, Agent, or Firm*—Sterne, Kessler, Goldstein & Fox P.L.L.C.

(57) ABSTRACT

The invention relates to a process for the synthesis of d-(17α)-13-ethyl-17-hydroxy-18,19-dinorpregn-4-ene-20-yn-3-one-oxime (also known as norelgestromin) via acetylation of d-norgestrel at position 17; oximation of the oxo group at position 3 of the obtained d-(17α)-13-ethyl-17-(acetyloxy)-18,19-dinorpregn-4-ene-20-yn-3-one; and then hydrolyzing the acetyloxy group at position 17 of the obtained d-(17α)-13-ethyl-17-(acetyloxy)-18,19-dinorpregn-4-ene-20-yn-3-oxime derivative, thereby obtaining norelgestromin.

14 Claims, No Drawings

FOREIGN PATENT DOCUMENTS

| | | |
|---|---|---|
| EP | 0 063 369 | 10/1982 |
| EP | 0 309 263 | 3/1989 |
| GB | 1123104 | 8/1968 |
| GB | 1 452 179 | 10/1976 |
| HU | 165356 | 8/1974 |
| HU | 183397 | 4/1984 |
| HU | 185797 | 3/1985 |
| WO | WO 96/40087 | 12/1996 |
| WO | WO 96/40355 | 12/1996 |
| WO | WO 2005/000867 | 1/2005 |
| WO | WO 2005/000868 | 1/2005 |

OTHER PUBLICATIONS

Derwent World Patent Index, Dialog File 351, English Language Abstract for Austrian Patent No. AT 348 151 (Document AO2), Accession No. 1001052, 2005.

STNEasy from CAplus, Accession No. 1967:105091, English Language Abstract of: Rufer, C., et al., "Totalsynthese von optisch aktiven 13-Äthyl-gonan-Derivaten," *Liebigs Annalen der Chemie 702*:141-148, Verlag Chemie (1967) (Document AS8).

International Search Report for International Patent Application No. PCT/HU2004/000030, mailed Oct. 15, 2004, European Patent Office, Rijswijk, Netherlands.

Written Opinion of the International Searching Authority for International Patent Application No. PCT/HU2004/000030, mailed Oct. 15, 2004, European Patent Office, Munich, Germany.

International Search Report for International Patent Application No. PCT/HU2004/000031, mailed Oct. 11, 2004, European Patent Office, Rijswijk, Netherlands.

Written Opinion of the International Searching Authority for International Patent Application No. PCT/HU2004/000031, mailed Oct. 11, 2004, European Patent Office, Rijswijk, Netherlands.

Derwent WPI, Dialog File No. 351, Accession No. 3545094, English language abstract for European Patent No. EP 0 063 369 (Document AO3), 2005.

Abrams, L.S., et al., "Pharmacokinetics of Norelgestromin and Ethinyl Estradiol from Two Consecutive Contraceptive Patches," *J. Clin. Pharmacol.* 41:1232-1237 American College of Clinical Pharmacology (2001).

Aicher, T.D., et al., "Triterpene and Diterpene Inhibitors of Pyruvate Dehydrogenase Kinase (PDK)," *Bioorganic Med. Chem. Letters*, 9:2223-2228 Elsevier Science Ltd. (1999).

Bringer, J., "Norgestimate: A clinical overview of a new progestin," *Am. J. Obstet. Gynecol. 166*: 1969-1977 Mosby-Year Book, Inc. (1992).

Ferenczi-Fodor, K., et al., "Separation and determination of steroid isomers on amino-bonded silica by conventional and overpressurized thin-layer chromatography," *J. Chromat. 392*: 464-469, Elsevier Science Publishers B.V. (1987).

Gazdag, M., et al., "Separation of Isomeric Compounds as Cyclodextrin Inclusion Complexes on a Cyanopropylsilica Stationary Phase," *J. Chromat. 371*:227-234 Elsevier Science Publishers B.V. (1986).

Hara, S., and Kitaro, O., "Synthesis and Characters of 1-Substituted A-Norsteroids," *Tetrahedron Letters 10*:1057-1061 Pergamon Press Ltd. (1966).

Hara, S., et al., "Quantitative Resolution of *Syn* and *Anti* Isomers of Steroidal $\alpha$, $\beta$-Unsaturated Oximes and O-methyloximes," *Chemistry & Industry 1*:832-833 (1967).

Herz, S., et al., "Esterification of Acid Chlorides with Thallium and Potassium Salts of 19-Norethisterone: Formation of 17-Enol Esters," *Steroids 40*:261-266 Holden-Day, Inc. (1982).

Leung, S.L., et al., "Norethisterone and Levonorgestrel Esters: A Novel Synthetic Method," *Steroids 46*: 639-647 Holden-Day, Inc. (1985).

McGuire, J.L., et al., "Pharmacologic and pharmacokinetic characteristics of norgestimate and its metabolites," *Am. J. Obstet. Gynecol.* 163:2127-2131 Mosby-Year Book, Inc. (1990).

Pasqualini, J.R., et al., "Norelgestromin as selective estrogen enzyme modulator in human breast cancer cell lines. Effect on sulfatase activity in comparison to medroxyprogesterone acetate," *J. Steroid Biochem. & Mol. Biol. 84*:193-198 Elsevier Science Ltd. (Feb. 2003).

Patthy, M., and Tomori, E., "High-Performance Liquid Chromatography and Gas-Liquid Chromatography of Some Norgestrel Intermediates. Physical Properties of Isolated *SYN*- and *ANTI*-Isomers of Oximes," *J. Chromat. 191*:145-154 Elsevier Scientific Publishing Company (1980).

Petersen, R.V., et al., "Controlled Release of Progestins From poly($\alpha$-Amino Acid) Carriers," *Controlled Release Bioactive Materials* :45-60 Academic Press (1980).

Quinkert, G., et al., eds. "(−)-Norgestrel," *Synform 3*:19-32, VCH Verlagsgesellschaft (1985).

Shroff, A.P., et al., "Synthesis and Antifertility Activity of Some Oximinoandrostenes," *J. Med. Chem.*, 16:113-115 American Chemical Society (1973).

Szentesi, A., et al., "Determination of Circular Dichroism and Ultraviolet Spectral Parameters of Norgestimate- and Other $\Delta^4$-3-Ketosteroid Oxime Isomers Via Normal Phase HPLC Method," *Curr. Med. Chem.* 8:1341-1347 Bentham Science Publishers Ltd. (2001).

Ortho-McNeil Pharmaceutical, inc., "Ortho Evra™ (Norelgestromin/Ethinyl Estradiol Transdermal System)," Product Information, Ortho-McNeil Pharmaceutical, Inc., Raritan, NJ., 8 pages (2001).

Ortho-McNeil Pharmaceutical, inc., "Ortho Tri-Cyclen® Tablets, Ortho-Cyclen® Tablets (norgestimate/ethinyl estradiol)," Product Information, Ortho-McNeil Pharmaceutical, Inc., Raritan, NJ., 6 pages (2001).

Derwent English language abstract, Accession No. 1979-70047B, for DD 136502 (Document AN1).

STNEasy Database, Accession No. 1982:582735, English language abstract for CA1122592 (Document AO1).

Co-pending U.S. Appl. No. 10/879,710, inventors Tuba, Z., et al., filed Jun. 30, 2004 (Not Published).

\* cited by examiner

PROCESS FOR THE SYNTHESIS OF HIGH PURITY D-(17α)-13-ETHYL-17-HYDROXY-18,19-DINORPREGN-4-ENE-20-YN-3-ONE-OXIME

CROSS REFERENCE TO RELATED APPLICATIONS

Priority under 35 U.S.C. §119(a)-(d) is hereby claimed to Hungarian patent application No. P 03 01982, filed Jun. 30, 2003, and to Hungarian patent application No. P 03 01981, filed Jun. 30, 2003, both of which are incorporated by reference in their entireties.

BACKGROUND OF THE INVENTION

1. Field of the Invention

The invention relates to a process for the synthesis of high purity d-(17α)-13-ethyl-17-hydroxy-18,19-dinorpregn-4-ene-20-yn-3-one-oxime (also known as norelgestromin) comprising acetylation of d-norgestrel at position 17; oximation of the oxo group at position 3 of the obtained d-(17α)-13-ethyl-17-(acetyloxy)-18,19-dinorpregn-4-ene-20-yn-3-one; and then hydrolyzing the acetyloxy group at position 17 of the obtained d-(17α)-13-ethyl-17-(acetyloxy)-18,19-dinorpregn-4-ene-20-yn-3-oxime derivative.

2. Background Art

The investigation of the metabolism of norgestimate is described in *Am. J. Obstet Gynecol.* 163:2127-31. (1990). The authors disclosed that, after oral administration, the metabolites of d-norgestimate include norelgestromin, d-(17α)-13-ethyl-17-(acetyloxy)-18,19-dinorpregn-4-ene-20-yn-3-one (d-norgestrel acetate), and d-(17α)-13-ethyl-17-hydroxy-18,19-dinorpregn-4-ene-20-yn-3-one (d-norgestrel), all of which have some biological activity.

The efficacy and safety of norgestimate/ethinyl estradiol used as a third generation contraceptive are described in *Am. J. Obstet. Gynecol.* 166:1969-1977. (1992). That same article reports that the main metabolite of norgestimate is norelgestromin, which has a similar pharmacological profile, than norgestimate. After oral administration, norelgestromin is detectable in the blood serum after a short period of time.

U.S. Pat. No. 5,876,746 describes the use of norelgestromin, either alone or in combination with an estrogen component, in a transdermal patch to inhibit fertility.

Hungarian Patent No. 165356 describes the synthesis of dl- as well as d-norgestrel. The starting material of the synthesis is the racemic or the optically active 13-ethyl-3-methoxy-gona-2,5(10)-diene-17β-ol, which is reacted with hydroxylammonium chloride in pyridine at 100° C. Then the obtained 13-ethyl-3-(hydroxyimino)-gon-4-ene-17β-ol is oxidized at position 17, followed by ethinylation of the oxo group at position 17, to give the dl-(17α)-13-ethyl-17-hydroxy-18,19-dinorpregn-4-ene-20-yn-3-one-oxime, or norelgestromin. Although the synthesis of the intermediates, the dl-(17α)-13-ethyl-17-hydroxy-18,19-dinorpregn-4-ene-20-yn-3-one-oxime and norelgestromin, are described, the identification and the purity (the quality requirements) as well as the pharmacological activity of these compounds are not provided.

U.S. Pat. No. of 4,027,019 describes the synthesis of the 17-acetoxy and the ester derivatives of norelgestromin in general, as well as the pharmacological activity thereof.

BRIEF SUMMARY OF THE INVENTION

Meeting the increasingly demanding requirements of pharmaceutical regulatory agencies is a basic requirement for every active ingredient approved for therapy, including steroids having high biological activity. The present invention provides an economical process for producing high purity norelgestromin sufficient to meet standards of these regulatory agencies. In certain embodiments, this high purity norelgestromin meets even more stringent requirements as well.

In one embodiment, the present invention is directed to a process for the synthesis of d-(17α)-13-ethyl-17-hydroxy-18,19-dinorpregn-4-ene-20-yn-3-one-oxime (also known as norelgestromin) comprising acetylation of d-norgestrel at position 17; oximation of the oxo group at position 3 of the obtained d-(17α)-13-ethyl-17-(acetyloxy)-18,19-dinorpregn-4-ene-20-yn-3-one; and then hydrolyzing the acetyloxy group at position 17 of the obtained d-(17α)-13-ethyl-17-(acetyloxy)-18,19-dinorpregn-4-ene-20-yn-3-oxime derivative, thereby obtaining d-(17α)-13-ethyl-17-hydroxy-18,19-dinorpregn-4-ene-20-yn-3-one-oxime. In certain embodiments, the process yields high purity d-(17α)-13-ethyl-17-hydroxy-18,19-dinorpregn-4-ene-20-yn-3-one-oxime.

In another embodiment, the present invention is directed to a composition, such as a pharmaceutical composition, comprising high purity norelgestromin. In certain aspects, the invention also includes a composition comprising norelgestromin prepared according to the above recited process.

In another embodiment, the present invention is directed to a method of providing contraception of hormone replacement therapy by administering a pharmaceutical composition comprising high purity norelgestromin made according to the process described herein.

DETAILED DESCRIPTION OF THE INVENTION

Surprisingly it was found that norelgestromin can be prepared having a purity an order of magnitude more pure than the purity limit (maximum amount of impurity is less than 1%) usually provided in pharmacopoeias.

In one embodiment, the present invention relates to a process for the synthesis of d-(17α)-13-ethyl-17-hydroxy-18,19-dinorpregn-4-ene-20-yn-3-one-oxime (also known as norelgestromin), preferably of high purity, comprising acetylation of d-norgestrel at position 17, oximation of the oxo group at position 3 of the obtained d-(17α)-13-ethyl-17-(acetyloxy)-18,19-dinorpregn-4-ene-20-yn-3-one; and then hydrolyzing the acetyloxy group at position 17 of the obtained d-(17α)-13-ethyl-17-(acetyloxy)-18,19-dinorpregn-4-ene-20-yn-3-oxime derivative. In a preferred embodiment, the process further comprises purifying by recrystallization the d-(17α)-13-ethyl-17-(acetyloxy)-18,19-dinorpregn-4-ene-20-yn-3-one obtained from the acetylation step.

In another embodiment of the present invention, the process further comprises a step of making the E or Z oxime isomer of norelgestromin in high purity. According to this embodiment, the geometrical isomers are separated from the anti-syn isomeric mixture formed in the oximation step before the hydrolysis using known methods. Such methods include, for example, chromatography. The obtained compounds are subsequently hydrolyzed. The hydrolysis according to the present invention does not substantially affect the geometry of the double bond of the oxime. Accordingly, after the hydrolysis, the appropriate pure or substantially pure anti and syn isomers of norelgestromin are obtained. In another embodiment, the E and Z oxime isomers are separated after the final hydrolysis step. For example, the E and Z isomers can be separated by chromatography.

In a first step in one embodiment of the invention, d-norgestrel is acetylated at position 17. Various methods of acetylating d-norgestrel at position 17 can be used in the present invention. For example, suitable reagents for acetylation include acetic anhydride along with a suitable catalyst. Preferred catalysts include acid catalysts, include Lewis acid catalysts such as zinc chloride. In another embodiment, perchloric acid is used in the acetylation step. In one embodiment of the present invention, the acetylation step comprises reacting d-(17α)-17-hydroxy-13-ethyl-18,19-dinorpregn-4-ene-20-yn-3-one with acetic anhydride in acetic acid in the presence of zinc chloride and hydrogen chloride. In another embodiment, the acetylation step comprises reacting d-(17α)-17-hydroxy-13-ethyl-18,19-dinorpregn-4-ene-20-yn-3-one with acetic anhydride in acetic acid in the presence of perchloric acid, e.g., 70% perchloric acid. In a preferred embodiment, the acetylation is performed in an inert atmosphere, for example, under a nitrogen or argon atmosphere. The excess acetic anhydride and a "enol acetate" byproduct can be decomposed with an acid, for example, aqueous hydrochloric acid.

In one embodiment, the acetylating agent, for example acetic anhydride, is used in a ratio of about 1 to about 5 moles per mole of starting d-norgestrel. In another embodiment, the acetylating agent is used in a ratio of about 2 to about 3 moles per mole of staring d-norgestrel. In another embodiment, the acetylating agent is used in a ratio of about 1, 1.2, 1.4, 1.6, 1.8, or 2 moles per mole of starting d-norgestrel.

In one embodiment, a suitable acid is used in the acetylation step. Such acids include, but are not limited to, aluminum halides, zinc halides, tin halides, p-toluenesulfonic acid, hydrochloric acid, and the like.

The acetylation step is preferably performed in a solvent. In one embodiment, the solvent used is acetic acid, for example glacial acetic acid. In other embodiments, the solvent used is an inert solvent or mixture of solvents comprising one or more of dichloromethane, chloroform, carbontetrachloride, benzene, toluene, tetrahydrofuran, or other solvents known in the art.

The d-(17α)-17-(acetyloxy)-13-ethyl-18,19-dinorpregn-4-ene-20-yn-3-one can be purified after the acetylation step. The compound can be purified using techniques known to one of ordinary skill in the art. Such techniques include chromatography, flash chromatography, recrystallization, filtration, and the like. Additionally, the d-(17α)-17-(acetyloxy)-13-ethyl-18,19-dinorpregn-4-ene-20-yn-3-one can be isolated by addition of water to the reaction mixture and then filtered as a solid material. The solid material can be recrystallized. In another embodiment, the solid material is purified by chromatography. In one example, the d-(17α)-17-(acetyloxy)-13-ethyl-18,19-dinorpregn-4-ene-20-yn-3-one is isolated from the reaction mixture by addition of ice-water; the precipitated product is filtered off, washed with water until neutral, dried, and dissolved in a suitable solvent, such as but not limited to dichloromethane, acetone, butanone, chloroform, toluene, and mixtures thereof; and purified with silica gel or alumina and/or charcoal. In a preferred embodiment, after filtration of the adsorbents, the solution comprising the d-(17α)-17-(acetyloxy)-13-ethyl-18,19-dinorpregn-4-ene-20-yn-3-one is concentrated, and the residue is preferably recrystallized. In a further preferred embodiment, the solvent used for recrystallization is a mixture of diisopropyl ether and acetonitrile or a mixture of diisopropyl ether and ethanol. In preferred embodiments, the recrystallization solvent used is a mixture of approximately 9:1 diisopropyl ether/acetonitrile or a mixture of approximately 9:1 diisopropyl ether/ethanol. Other solvents can be used for the recrystallization and include but are not limited to diethyl ether, chloroform, ethyl acetate, toluene, isopropanol, ethanol, other inert solvents known in the art, and mixtures thereof.

In another embodiment of the acetylation step, the reaction mixture is stirred, for example, for about 5 to about 100 minutes, preferably about 10 to about 30 minutes, more preferably about 20 minutes; then water and 10% aqueous HCl is added to the reaction mixture. The water and aqueous HCl can be added in various amounts, for example in a ratio of about 1:1 to about 5:1, or about 2:1. The exact amount of water and HCl added can vary, although in one embodiment, about 250 mL to about 300 mL of water is added per mole of norgestrel starting material. The resulting solution is then stirred, for example for at least about 30 minutes, about 1 hour, or about 2 hours. After stirring, the reaction mixture is poured into ice water or onto ice. The precipitated product is then isolated according to standard procedures, for example, filtered off, washed with water, and dried. The obtained crude d-norgestrel acetate can then be further purified, for example, dissolving in a suitable solvent and removing impurities with an adsorbant. For example, in one embodiment, the d-norgestrel acetate is dissolved in dichloromethane and stirred with silica gel. The slurry is stirred for a time sufficient to remove impurities, for example 30 minutes, although the precise length of stirring can vary. The adsorbant is then filtered off, and the solvent is evaporated. The residue (d-norgestrel acetate) is dissolved in a solvent, for example, refluxed with a 9:1 mixture of isopropyl ether/acetonitrile, for a time sufficient to dissolve the d-norgestrel acetate, for example about 15 minutes. The solution is then cooled to allow precipitation of the d-norgestrel acetate. In one embodiment, the solution is cooled to about 0° C. In other embodiments, the solution is cooled between about 0° C. to about 15° C.

In another embodiment, the mother liquor from the recrystallization of the d-norgestrel acetate can be used to obtain additional d-norgestrel acetate by repeating the purification process.

In another embodiment of the acetylation step, to a stirred suspension of d-norgestrel (having a purity of at least 90%) in acetic acid, acetic anhydride, anhydrous zinc chloride, and a solution of HCl in acetic acid are added. In certain embodiments, the ratio of d-norgestrel to acetic anhydride is about 1:1 to about 3:1, preferably about 2:1; other ratios are used in other embodiments. The reaction mixture is stirred, for example, for about 5 to about 30 minutes, e.g., about 20 minutes. Then water and acid, e.g., HCl, are added with further stirring, for example, for about 30 minutes to about 1 hour. The reaction mixture is then poured into ice or ice-water mixture and purified as described herein.

In certain embodiments, the d-norgestrel acetate prepared has a purity of at least 99%. In other embodiments, the d-norgestrel acetate prepared has a purity of at least 90%, 95%, 96%, 97%, or 98%.

In another step of the process of the invention, d-(17α)-17-(acetyloxy)-13-ethyl-18,19-dinorpregn-4-ene-20-yn-3-one is reacted in an oximation reaction to form d-(17α)-17-(acetyloxy)-13-ethyl-18,19-dinorpregn-4-ene-20-yn-3-one-oxime. Various methods of converting d-(17α)-17-(acetyloxy)-13-ethyl-18,19-dinorpregn-4-ene-20-yn-3-one to d-(17α)-17-(acetyloxy)-13-ethyl-18,19-dinorpregn-4-ene-20-yn-3-one-oxime can be used in the present invention. In one embodiment, the obtained d-(17α)-17-(acetyloxy)-13-ethyl-18,19-dinorpregn-4-ene-20-yn-3-one is reacted with an oximation reagent, such as but not limited to hydroxylammonium acetate and hydroxylammonium chloride. In another embodiment, the d-(17α)-17-(acetyloxy)-13-ethyl-18,19-dinorpregn-4-ene-20-yn-3-one is reacted with hydroxylammonium acetate or hydroxylammonium chloride in the presence of sodium acetate in acetic acid.

The exact ratios of the reagents used in the oximation step may vary. For example, certain embodiments employ a ratio of hydroxylammonium acetate to d-norgestrel acetate of about 1:1 to about 5:1. Other suitable ratios include about 2:1 and about 3:1. In other embodiments, hydroxylammonium chloride is used in a ratio of about 1:1 to about 10:1 relative to the starting d-norgestrel acetate. Other suitable ratios of hydroxylammonium chloride to d-norgestrel acetate include about 5:1, about 6:1, and about 7:1.

Any number of oximation reagents can be used in accordance with the present invention. Such oximation reagents include but are not limited to hydroxylammonium salts in conjunction with a base. Bases can include acetate, pyridine, and the like.

In certain embodiments, the oximation reaction is preferably performed under an inert atmosphere, such as nitrogen or argon. The reaction mixture can be stirred until the reaction is complete. In a preferred embodiment, the oximation proceeds for about 30 minutes to about 100 minutes, preferably about 45 minutes. In another embodiment, the oximation reaction is allowed to proceed for about 1 hour. The precise length of the reaction is not critical. In a preferred embodiment, the reaction is stirred until complete or substantially complete. The reaction mixture is then worked up using standard procedures. For example, in one embodiment, after the reaction is complete, water is added to the reaction mixture. The precipitated product is then filtered off, washed with additional water, and then dried. In a further embodiment, the product is recrystallized from a suitable solvent, such as ethanol or isopropanol.

In another step of one embodiment of the process of the invention, d-(17α)-17-(acetyloxy)-13-ethyl-18,19-dinorpregn-4-ene-20-yn-3-one-oxime is hydrolyzed to obtain d-(17α)-17-hydroxy-13-ethyl-18,19-dinorpregn-4-ene-20-yn-3-one-oxime. In one embodiment, the d-(17α)-17-(acetyloxy)-13-ethyl-18,19-dinorpregn-4-ene-20-yn-3-one-oxime is hydrolyzed with an equivalent of a metal hydroxide in a solution containing a $C_1$-$C_4$ alkanol. In certain embodiments, the hydrolysis is carried out under an inert atmosphere, for example a nitrogen or argon atmosphere. In another embodiment, the reaction is carried out at a temperature from about 5° C. to about 35° C. The reaction mixture can be stirred, preferably vigorously. The precise length of the reaction is not critical. In a preferred embodiment, the reaction is stirred until complete or substantially complete. Suitable $C_1$-$C_4$ alkanols include methanol, ethanol, propanol, and butanol.

A number of metal hydroxides can be used to hydrolyze the acetyloxy group. Suitable hydroxides include, but are not limited to, sodium hydroxide, potassium hydroxide, lithium hydroxide, barium hydroxide, and lithium hydroxide monohydrate.

After the hydrolysis reaction is complete, the product is isolated using known or standard techniques and procedures. For example, in one embodiment, the mixture is diluted with water, and the pH of the resulting suspension is adjusted to about 7.5 to about 9 with a suitable acid, such as acetic acid; the precipitated product is filtered off, washed with water until neutral, and dried; the crude product is dissolved in ethanol, decolorized with charcoal, and after filtration of the charcoal water is added to the obtained solution, the precipitated high purity d-(17α)-17-hydroxy-13-ethyl-18,19-dinorpregn-4-ene-20-yn-3-one-oxime is filtered off, washed with water, and, in certain embodiments, recrystallized from ethanol.

In another embodiment, the present invention is directed to a process of preparing high purity norelgestromin, comprising hydrolyzing d-(17α)-17-(acetyloxy)-13-ethyl-18,19-dinorpregn-4-ene-20-yn-3-one-oxime with an equivalent of an alkali metal hydroxide in a $C_1$-$C_4$ alkanol solution under an inert atmosphere at a temperature of about between a temperature of 5-35° C.; diluting the reaction mixture with water after the reaction is complete; adjusting the pH of the resulted suspension to about 7.5 to about 9 with an acid, for example hydrochloric acid, acetic acid, the like, and mixtures thereof; filtering off the precipitated norelgestromin; washing with the precipitated norelgestromin with water; drying the precipitated norelgestromin; and recrystallizing the norelgestromin.

In a further embodiment, the process further comprises dissolving the precipitated norelgestromin in a suitable solvent, such as ethanol, isopropanol, or mixtures thereof; decolorizing the solution of norelgestromin with a suitable decolorizing agent, such as charcoal; after filtration of the decolorizing agent, adding water to the solution of norelgestromin; and filtering off the precipitated high purity d-(17α)-17-hydroxy-13-ethyl-18,19-dinorpregn-4-ene-20-yn-3-one-oxime.

In another embodiment, the invention is directed to a process for preparing high purity d-(17α)-13-ethyl-17-hydroxy-18,19-dinorpregn-4-ene-20-yn-3-one-oxime comprising acetylating d-(17α)-17-hydroxy-13-ethyl-18,19-dinorpregn-4-ene-20-yn-3-one having a purity of at least 93%, with acetic anhydride in acetic acid, in the presence of zinc chloride and hydrogen chloride in an inert gas atmosphere; after the reaction is complete, adding aqueous hydrochloric acid to the reaction mixture; isolating the formed d-(17α)-17-(acetyloxy)-13-ethyl-18,19-dinorpregn-4-ene-20-yn-3-one from the reaction mixture by addition of ice-water, filtering off the precipitated product, washing with water until neutral, drying, dissolving in dichloromethane or acetone, and purifying with silica gel or alumina and charcoal, concentrating the resulted solution after filtration of the adsorbents and recrystallizing the residue from a 9:1 mixture of diisopropyl ether/acetonitrile or diisopropyl ether/ethanol; reacting the obtained d-(17α)-17-(acetyloxy)-13-ethyl-18,19-dinorpregn-4-ene-20-yn-3-one either with hydroxylammonium acetate, or with hydroxylammonium chloride in the presence of sodium acetate; in acetic acid in a nitrogen atmosphere under vigorous stirring for about 45 minutes, to form d-(17α)-17-(acetyloxy)-13-ethyl-18,19-dinorpregn-4-ene-20-yn-3-one-oxime; adding water after the reaction is complete, filtering, washing with water, drying, and recrystallizing the d-(17α)-17-(acetyloxy)-13-ethyl-18,19-dinorpregn-4-ene-20-yn-3-one-oxime from ethanol; hydrolyzing the obtained d-(17α)-17-(acetyloxy)-13-ethyl-18,19-dinorpregn-4-ene-20-yn-3-one-oxime with an equivalent of an alkali metal hydroxide in a $C_1$-$C_4$ alkanol solution, under nitrogen atmosphere between a temperature of 5-35° C., under vigorous stirring, diluting the reaction mixture with water after the reaction is complete and adjusting the pH of the resulted suspension to 7.5-9 with acetic acid, filtering off the precipitated product, washing with water, drying, dissolving the crude product in ethanol, decolorizing with charcoal, and adding water after filtration of the charcoal to the obtained solution, filtering off the precipitated high purity d-(17α)-17-hydroxy-13-ethyl-18,19-dinorpregn-4-ene-20-yn-3-one-oxime, washing with water and optionally recrystallizing from ethanol. The hydrolysis of d-(17α)-17-(acetyloxy)-13-ethyl-18,19-dinorpregn-4-ene-20-yn-3-one-oxime can be effected with, for example, lithium hydroxide monohydrate in methanol. In an alternative embodiment, the acetylation step is performed with acetic anhydride in acetic acid, in the presence of perchloric acid, preferably 70% perchloric acid, in an inert gas atmosphere.

Each of the acetylation, oximation, and hydrolysis reactions are performed under an inert atmosphere in certain embodiments. For example, the reactions are performed under an atmosphere of nitrogen or argon. Such techniques are known to one of ordinary skill in the art.

In a yet further embodiment, the present invention is directed to a process of preparing high purity norelgestromin comprising:

the starting material, d-(17α)-17-hydroxy-13-ethyl-18,19-dinorpregn-4-ene-20-yn-3-one (d-norgestrel), preferably having a purity of at least 93% or 94%, is acetylated with acetic anhydride in acetic acid, in the presence of zinc chloride and hydrogen chloride, or 70% perchloric acid, in an inert gas atmosphere, and after the reaction is complete the excess of acetic anhydride and the "enol acetate" byproduct are decomposed with aqueous hydrochloric acid; then the formed d-(17α)-17-(acetyloxy)-13-ethyl-18,19-dinorpregn-4-ene-20-yn-3-one is isolated from the reaction mixture by addition of ice-water, the precipitated product is filtered off, washed with water until neutral, dried, dissolved in dichloromethane or acetone and purified with silica gel or alumina and charcoal, after filtration of the adsorbents the resulted solution is concentrated and the residue is preferably recrystallized from a 9:1 mixture of diisopropyl ether/acetonitrile or diisopropyl ether/ethanol; the obtained d-(17α)-17-(acetyloxy)-13-ethyl-18,19-dinorpregn-4-ene-20-yn-3-one is reacted either with hydroxylammonium acetate or with hydroxylammonium chloride in the presence of sodium acetate, in acetic acid in nitrogen atmosphere under vigorous stirring for about 45 minutes, after the reaction is complete water is added, the precipitated product is filtered off, washed with water until neutral, dried and recrystallized preferably from ethanol; and the obtained d-(17α)-17-(acetyloxy)-13-ethyl-18,19-dinorpregn-4-ene-20-yn-3-one-oxime is hydrolyzed with an equivalent of an alkali metal hydroxide in a $C_1$-$C_4$ alkanol solution, in nitrogen atmosphere at a temperature of 5-35° C., under vigorous stirring, after the reaction is complete the mixture is diluted with water and the pH of the resulting suspension is adjusted to 7.5-9 with acetic acid, the precipitated product is filtered off, washed with water until neutral, dried, the crude product is dissolved in ethanol, decolorized with charcoal, and after filtration of the charcoal, water is added to the obtained solution, the precipitated high purity d-(17α)-17-hydroxy-13-ethyl-18,19-dinorpregn-4-ene-20-yn-3-one-oxime is filtered off, washed with water, and, in certain embodiments, recrystallized from ethanol.

In certain embodiments, the process of the present invention produces norelgestromin having a purity of at least 99.5 mass percent, and the overall impurity of other steroids is not more than 0.1 mass percent. In another embodiment, the process of the invention produces norelgestromin having a purity of at least 99.9 mass percent. In another embodiment, the high purity norelgestromin contains less than 1% of impurity as calculated based on d-norgestrel acetate. In other embodiments, the process of the present invention produces norelgestromin having a purity of at least 90%, 95%, 96%, 97%, or 98%.

Another aspect of the present invention relates to a process for preparing norelgestromin on a large scale. An advantage of the process described herein is that multigram quantities of norelgestromin, and its individual oxime isomers, can be prepared in a safe and economical fashion. The process of the invention can be readily adapted for industrial synthesis of norelgestromin for use in mass-produced pharmaceutical compositions. Furthermore, high purity norelgestromin can be produced on an industrial scale according to the present invention. For example, in one embodiment, the present invention is directed to a process for the synthesis of high purity d-(17α)-13-ethyl-17-hydroxy-18,19-dinorpregn-4-ene-20-yn-3-one-oxime (also known as norelgestromin) via acetylation of d-norgestrel at position 17, oximation of the oxo group at position 3 of the obtained d-(17α)-13-ethyl-17-(acetyloxy)-18,19-dinorpregn-4-ene-20-yn-3-one, and then hydrolyzing the acetyloxy group at position 17 of the obtained d-(17α)-13-ethyl-17-(acetyloxy)-18,19-dinorpregn-4-ene-20-yn-3-oxime derivative, thereby obtaining norelgestromin; wherein the yield of norelgestromin is at least 20 grams. In other embodiments, the yield of the process is at least about 10 grams, about 30 grams, and about 40 grams. In a preferred embodiment, the process further comprises recrystallizing the norelgestromin. In certain embodiments, the yield refers to the amount of product obtained from a single batch. In other embodiments, the process according to the present invention produces high purity norelgestromin in a yield of between 10 grams to about 50 grams. In other embodiments, the process produces an intermediate in multigram quantities.

It is understood that the process as described herein can be used as a part of another process comprising further steps. For example, the invention further comprises, in certain embodiments, one or more additional steps for producing the d-(17α)-17-hydroxy-13-ethyl-18,19-dinorpregn-4-ene-20-yn-3-one which is used in the acetylation step described herein. Alternatively, the process of the invention may comprise further steps that use the norelgestromin as an intermediate.

In another embodiment, the process described herein can be used in conjunction with, as a part of, or in addition to, in whole or in part, the process described in copending application Ser. No. 10/879,710 titled "Process of Making Isomers of Norelgestromin and Methods Using the Same," filed Jun. 30, 2004, which is incoporated herein by reference in its entirety. For example, a process described therein for preparing a substantially pure E or Z-isomer of norelgrestromin can be used in conjunction with the method described herein for preparing high purity norelgestromin. Additionally, any of the specific processes of hydrolyzing the acetyloxy group at position 17 of d-(17α)-13-ethyl-17-(acetyloxy)-18,19-dinorpregn-4-ene-20-yn-3-oxime derivative, described in the copending application can be used in conjuction with, or instead of, one or more steps of the process described herein.

Compositions

An additional aspect of the present invention is directed to a composition comprising high purity norelgestromin. A composition according to the present invention includes a pharmaceutical composition comprising high purity norelgestromin and one or more pharmaceutically acceptable excipients. Pharmaceutical compositions of the present invention may be formulated, as is well known in the prior art, such as by reference to known compilations as Remington's Pharmaceutical Sciences, Mack Publishing Co., Easton, Pa., USA.

In one embodiment, the invention is directed to a pharmaceutical composition comprising high purity norelgestromin and a pharmaceutically acceptable carrier and/or recipient. The amount of high purity norelgestromin present in the composition can vary but is generally an amount effective to treat a condition as described herein or known in the art. Other dosage amounts are described herein.

The pharmaceutical compositions of the invention can be administered to any animal that can experience the beneficial effects of the compounds of the invention. Foremost among such animals are humans, although the invention is not intended to be so limited. Preferably, the composition of the present invention is administered to a woman.

The pharmaceutical compositions of the present invention can be administered by any means that achieve their intended purpose. For example, administration can be by subcutaneous, intravenous, intramuscular, intraperitoneal, buccal, or ocular routes, rectally, parenterally, intrasystemically, intravaginally, topically (as by powders, ointments, drops or transdermal patch), or as an oral or nasal spray. The dosage administered will be dependent upon the age, health, and weight of the recipient, kind of concurrent treatment, if any, frequency of treatment, and the nature of the effect desired.

The pharmaceutical compositions of the present invention can preferably be tablets, dragèes, or transdermal patches. The tablets can contain, in addition to the active ingredients, the usual carriers. excipients. diluents, stabilizers, flavorings or aromatizing agents, as well as formulation promoting or formulation-providing additives. The formulation of tablets can be carried out by methods conventionally used in practice. The preparation of dragèes can be carried out, for example, by coating the dragèes cores, prepared similarly to tablets, according to the usual methods.

In one embodiment, the pharmaceutical composition of the present invention is a tablet comprising an amount of high purity norelgestromin effective to provide birth control or contraception.

In another embodiment, the dosage form is a tablet comprising high purity norelgestromin, for example about 0.1 to about 0.5 mg, preferably about 0.25 mg, and ethinyl estradiol, for example about 10 to about 50 μg, preferably about 35 μg. The tablet further comprises suitable excipients, such as lactose, microcrystalline cellulose, colloidal silicon dioxide (e.g., Aerosil® (Evonik Degussa GmbH Ltd., Hanau, DE)), and magnesium stearate.

In another embodiment, the tablet is formed by spray-drying a solution of high purity norelgestromin and ethinyl estradiol in solvent, such as ethanol, on a homogeneous mixture of lactose and cornstarch. The solvent is removed from the mixture by fluidization drying. The obtained powder mixture containing the active ingredients is granulated according to known methods and formed into tablets. Other suitable excipients include polyvinylpyrrolidone (PVP), colloidal silicon dioxide, and magnesium stearate.

In another embodiment, the pharmaceutical composition is a transdermal patch comprising high purity norelgestromin. The patches can preferably be matrix-type transdermal patches consisting of 3 layers. Their external layer is a membrane, which is impermeable to the active ingredients and other components of the matrix, consisting of PVC, polyethylene, polypropylene or polyurethane film. The matrix containing the active ingredients is disposed on this external layer. The matrix contains pressure sensitive adhesive component, which can be polyacrylate, polydimethylsiloxane or polyisobutylene. One of these adhesives is mixed with the active ingredients and the polyvinylpyrrolidone auxiliary material, which inhibits crystallization. Auxiliaries (enhancers), which promote the absorption of steroids through the skin, are preferably dispersed in the matrix as well. These components can be for example esters of aliphatic alcohols, such as lauryl lactate, oleic acid, etc. The so obtained dispersion is disposed on the external layer of the patch and dried. The matrix of the patch is covered by the third layer of the plaster, the protective layer, which can be for example a polyethylene terephthalate film. The protective layer should be removed before the application of the patch to the skin.

In other embodiments, the transdermal matrix comprises one or more permeation enhancers to increase the permeability of the high purity norelgestromin and the optional estrogen through the skin. Examples of skin permeation enhancers that may be included in the matrix are described in U.S. Pat. Nos. 5,059,426; 4,973,468; 4,906,463; and 4,906,169, each of which is fully incorporated by reference herein, and include, but are not limited to, lactate esters of $C_{12}$ to $C_{18}$ aliphatic alcohols, lauryl lactate, oleic acid, or polyethylene glycol monolaurate. The amount of permeation enhancer included in the matrix depends upon the particular enhancer(s) used. In most instances, then enhancer constitutes about 1 to about 20% by weight of the matrix.

Broadly, patches are devices that contain, at a minimum, a drug reservoir matrix for holding the drug and metering the drug deposition or delivery to the skin, a backing, and an adhesive layer for adhering the device to the patient. The device may contain other layers such as a drug release rate controlling layer for modulating delivery rate, and the like. The device may contain permeation enhancers to increase the rate of penetration of drugs across the skin. Patches are well known and understood by persons skilled in the art. Patches are now employed in marketed products for the administration of certain progestogens. Specific patches and even their application to steroids of the type described herein are described in U.S. Pat. Nos. 5,474,783; 5,656,286; 5,958,446; 6,024,976; 5,252,334; 5,006,342; and 4,906,463, each of which is fully incorporated by reference herein. Other suitable transdermal dosage forms are disclosed in Published U.S. Patent Appln. Pub. No. 20040043171, which is fully incorporated by reference herein.

In certain embodiments, the patch of the invention has a basal surface area (i.e., the area in diffusional contact with the skin) between 10 and 50 $cm^2$. Of course, various sizes and shapes of patches are understood to be within the scope of the present invention.

In one embodiment, the invention comprises a matrix type transdermal patch of 3 layers containing 6.0 mg of high purity norelgestromin and 0.75 mg of ethinyl estradiol. For every patch unit, the composition comprises 6.0 mg of high purity norelgestromin, 0.75 mg of ethinyl estradiol, 25 mg of polyvinylpyrrolidone, 20 mg of lauryl lactate, and 248 mg of polyisobutylene.

In another embodiment, the matrix type transdermal patch of 3 layers contains about 6.0 mg of high purity norelgestromin and about 0.75 mg of ethinyl estradiol. In another embodiment, the composition comprises 261 mg of polydimethylsiloxane and 17 mg of polyvinylpyrrolidone, 15 mg of methyl laureate, 6.0 mg of high purity norelgestromin, and 0.75 mg of ethinyl estradiol.

In one embodiment, the dosage form, preferably the transdermal form, comprises an amount of active ingredients such that about 150 μg to about 350 μg, preferably 175 μg to about 350 μg, of high purity norelgestromin, and about 5 μg to about 45 μg, preferably about 10 to about 35 μg, more preferably about 20 μg of ethinyl estradiol are delivered per day.

In another embodiment, the invention is directed to a transdermal patch for providing hormone replacement therapy in a woman comprising: a) a backing layer; and b) a non-acrylate containing matrix layer underlying the backing layer, the matrix layer comprising a mixture of high purity norelgestromin, an estrogen selected from the group consisting of ethinyl estradiol and 17-β-estradiol, lauryl lactate, and a pressure sensitive adhesive consisting essentially of polyisobutylene and an aliphatic tackifier, and being adapted to be in diffusional communication with the skin of a woman and to co-administer a therapeutic amount of said high purity norelgestromin and said estrogen to said skin.

Other suitable transdermal dosage forms include those described in U.S. Pat. Nos. 5,876,746; 5,972,377; and 6,071,531, each of which is fully incorporated by reference herein. The dosage forms disclosed in these patents can be used in accordance with the present invention by replacing the 17-deacetylnorgestimate with the high purity norelgestromin of the present invention.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is within the skill of the artisan, for example, by means of conventional mixing, granulating, dragèe-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Pharmaceutical excipients are well known in the art. Suitable excipients include fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethylstarch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragèe cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

In another embodiment, the composition of the present invention is a vaginal ring. Vaginal rings are generally devices having an elastomeric portion or body into which the active steroid is dispersed and which acts as a reservoir and meter for the diffusion of active to the lining of the vagina. The ring may be composed entirely of elastomer with steroid homogenously dispersed throughout as described in U.S. Pat. No. 3,545,397. The ring may have an inert inner core surrounded by an active containing elastomeric layer as described in U.S. Pat. No. 4,012,496. The ring may have an elastomeric active containing inner core surrounded by a thin elastomeric layer initially containing no active. The ring may have an inert core, surrounded by an active containing elastomeric layer and further surrounded by an elastomeric outer layer of variable thickness initially containing no active as described in U.S. Pat. No. 4,292,965. The elastomer, the layered design of the ring, its surface area, the concentration of active, the nature of the active, etc., all combine to determine the release rate of active. Rings are well known and understood by persons skilled in the art. Rings are now employed in marketed products for the administration of certain steroids. Other suitable rings include those described in U.S. Pat. Nos. 4,871,543 and 5,188,835, each of which is fully incorporated by reference herein.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, cyclodextrin inclusion complexes.

In other embodiments, the high purity norelgestromin is administered parenterally as an injectable dosage form in a physiologically acceptable diluent such as sterile liquids or mixtures thereof, including water, saline, aqueous dextrose and other pharmaceutically acceptable sugar solutions, alcohols such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) #400, a pharmaceutically acceptable oil, fatty acid, fatty acid ester or glyceride, or an acetylated fatty acid glyceride with or without the addition of a pharmaceutically acceptable surfactant, such as a soap or detergent, suspending agent such as pectin, carbomers, methylcellulose, hydroxypropylmethylcellulose, or carboxymethylcellulose, an emulsifying agent or pharmaceutical adjuvants. In all cases, the form must be sterile and must be fluid enough to provide easy syringability exists.

Pharmaceutically acceptable oils which are useful in the formulation herein include those of petroleum, animal, vegetable or synthetic origin, including peanut oil, soybean oil, sesame oil, cottonseed oil, olive oil, sunflower oil, petrolatum, and mineral oil. Fatty acids which may be used include oleic acid, stearic acid, and isostearic acid, while the fatty acid esters useful herein may include ethyl oleate and isopropyl myristate. Suitable soaps include fatty acid alkali metal, ammonium, and triethanolamine salts.

In addition, suspensions of the high purity norelgestromin as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400. Aqueous injection suspensions can contain substances that increase the viscosity of the suspension, for example, sodium carboxymethyl cellulose, sorbitol, and/or dextran. Optionally, the suspension may also contain stabilizers.

Liquid dosage forms of high purity norelgestromin for oral administration include pharmaceutically acceptable emulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Suspensions, in addition to the high purity norelgestromin, may contain suspending agents such as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for vaginal administration are in one embodiment suppositories which can be prepared by mixing the compounds of the present invention with suitable non-irritating excipients or carriers such as cocoa butter, polyethylene glycol or a suppository wax which are solid at room temperature but liquid at body temperature and therefore melt in the rectum or vaginal cavity and release the drugs.

In other embodiments, the compositions of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used.

Method of Treatment

In a further aspect of the invention, the compounds and compositions described herein are used to treat one or more ailments, conditions, diseases, or physiological states. The present invention comprises administering to a subject in need an effective amount of high purity norelgestromin.

In one embodiment, the high purity norelgestromin is adminstered via a transdermal patch. The transdermal patch of the invention provides contraception for females, preferably women. The patch is also suitable for hormone replacement therapy.

In certain embodiments, the patch delivers high purity norelgestromin and, optionally an estrogen, to the skin continuously for an extended time period, for example 1-7 days and preferably for 7 days.

In one embodiment, the effective dose of substantially pure high purity norelgestromin for inhibiting ovulation is normally in the range of about 150 to about 350 µg/day, preferably from about 175 to about 300 µg/day, and more preferably from about 175 to about 250 µg/day. The effective dose of estrogen for inhibiting ovulation depends on the particular estrogen being co-administered. For instance, when the estrogen is ethinyl estradiol, the dose is normally at least 10 µg/day, preferably from about 10 to about 35 µg/day, and most preferably approximately 20 µg/day. In other embodiments, the typical doses are from about 20 µg/day to about 200 µg/day, and preferably from about 30 jUg/day to 150 µg/day of ethinyl estradiol When the patches are worn for contraception, a patch will typically be placed on the skin on the fifth day of the menstrual cycle, and replaced as needed until 21 days of wearing have elapsed. For instance, in the case of a 7-day patch, three patches will be required to deliver the drug(s) for the 21-day period. If desired a placebo patch may be worn thereafter until the fifth day of the succeeding menstrual cycle. This regimen is repeated for each menstrual cycle.

In certain embodiments, an effective amount administered is from about 150 to about 350 µg/day and preferably from about 175 to about 300 µg/day of high purity norelgestromin. In one aspect, the high purity norelgestromin is co-administered with an ovulation inhibiting amount of an estrogen, such as ethinyl estradiol. In other embodiments, an effective amount is from about 150 to about 350 µg/day and preferably from about 175 to 300 µg/day of high purity norelgestromin and from 10 to 35 µg/day of ethinyl estradiol.

In one embodiment, the composition of the present invention is intravaginally administered, by use of a ring. Broadly, rings are devices having an elastomeric portion or body into which the active steroid is dispersed and which acts as a reservoir and meter for the diffusion of active to the lining of the vagina.

In one embodiment, the contraceptive regimen according to the present invention is a progestin-only contraceptive regimen in which the high purity norelgestromin is continuously administered in a sufficient dose to have a contraceptive effect, and the regimen is administered cycle after cycle to a menstruating female to achieve a long term contraceptive effect. In such regimens, no estrogen is administered, and there is no period of time without hormone administration to allow for menstruation. Menstruating female is intended to refer to fertile women of child-bearing age. The method of administration might be transdermal, vaginal, or oral. Where administration is transdermal, a suitable patch is continuously worn with replacement as required. Where administration is vaginal, a suitable vaginal device, such as a ring, is continuously inserted with replacement as required. Where administration is oral, daily oral dosage units are administered.

In certain embodiments, the cycle of administration usually lasts 28 days or more, but it may be longer, for example up to 60 and even 90 days, or shorter down to 21 days. The cycle optionally includes a regimen in which there is a day to day or week to week variation in the dose of high purity norelegestromin administered according to a set pattern. In such a case the regimen, including variation of dose, is repeated in cycle following cycle. Alternatively, the cycle may also be a regimen in which there is no variation in the dose of the active administered. In such a case, the cycle is a convention representing a convenient unit of administration or sale. In either case, a contraceptive product utilizing the contraceptive regimen in question is prescribed, sold, and administered in units of cycles. The contraceptive product based on a cycle might be 1 to 10 of vaginal rings that are inserted and then replaced every 7, 14, or 21 days according to their design. The contraceptive product based on a cycle might be 2 to 10 transdermal patches that are attached and then replaced every 7, 10, or 14 days according to their design. The contraceptive product based on a cycle might be 21, 28, 56, or more tablets that are orally administered daily.

In the case of a daily oral tablet, there is administered in certain embodiments a preferred dose of high purity norelgestromin between about 30 µg to about 500 µg and more preferably between about 150 µg to about 300 µg. Specific daily oral tablets contain, for example, 100, 125, 180, 215, or 250 µg of high purity norelgestromin. In the case of a vaginal ring, a certain embodiment of a ring delivers to systemic circulation a daily dose of high purity norelgestromin between about 20 µg to about 300 µg and more preferably between about 90 µg to about 200 µg. A specific vaginal ring might be inserted for one week and deliver to systemic circulation in that period of time an average daily dose of 60, 75, 100, 125 or 150 µg of high purity norelgestromin. In the case of a transdermal patch, a preferred patch delivers to systemic circulation a daily dose of high purity norelgestromin between about 20 µg to about 300 µg and more preferably between about 90 jig to about 200 µg. A specific patch might be worn for one week and deliver to systemic circulation in that period of time an average daily dose of 60, 75, 100, 125, or 150 μg of high purity norelgestromin.

Other suitable regimens are disclosed in U.S. Published Patent Applications Pub. Nos. 20030229057; 20030225048; 20030225047; and 20030219471, each of which is fully incorporated by reference herein, and can be adapted to deliver the high purity norelgestromin In one embodiment, the high purity norelgestromin is administered in an amount effective to produce a contraceptive effect. According to another embodiment of the present invention, the high purity norelgestromin is administered in an amount which is an effective breast protective amount. In one embodiment, high purity norelgestromin is administered in an amount such that it is at least equivalent in both contraceptive and breast protecting effect to about 0.030 mg to about 0.750 mg of orally administered norgestimate. In another characterization of a breast protective amount of high purity norelgestromin, there is administered sufficient active compound to provide for, during a substantial portion of each day, a substantial suppression of sulfatase activity, for example, of 50% or greater and preferably of 67% or greater and most preferably of 75% or greater. A substantial portion of a day is intended to mean a period of at least 4 hours, but within the invention might mean a period of at least 8 hours or 12 hours or even 24 hours.

In another embodiment, the invention provides a method of treating a female in need of hormone replacement therapy comprising transdermally administering to said female a pharmaceutical patch regimen series consisting essentially of a series of transdermal patches arranged in alternating phases of dominant hormone activity of from about one day to about four days, said phases being selected from estrogen dominant activity phases and progestin dominant activity phases, each of said phases comprising at least one patch which is applied and removed in accordance with the particular dominant phase activity, wherein the estrogen dominant activity phase contains an amount of a substance exhibiting estrogen activity sufficient to promote the development of progestin receptors in the endometrium of said female, or an amount of a substance exhibiting estrogen activity sufficient to promote the development of progestin receptors in the endometrium of said female and an amount of a substance exhibiting progestin activity; and wherein the progestin dominant activity phases contain an amount of a substance exhibiting estrogen activity and an amount of substantially pure high purity norelgestromin sufficient to antagonize the effect of estrogen on the endometrium of said female, and the estrogen and progestin are selected from transdermally administrable hormones. Such a general method is described in further detail in U.S. Pat. No. 5,422,119, which is hereby fully incorporated by reference herein.

The present invention also provides a method of hormone replacement therapy. The high purity norelgestromin can be used in a suitable hormone replacement therapy regimen, either alone or in combination with other hormones. For example, in one embodiment, the method provides from about 150 to about 350 μg/day, and preferably from about 175 to about 300 μg/day high purity norelgestromin co-administered with from about 5 to about 45 μg/day and preferably from about 10 to about 35 μg/day of an ethinyl estradiol. In an alternative embodiment, the method provides from about 200 to about 350 μg/day, and preferably from about 175 to about 300 μg/day of high purity norelgestromin co-administered with from about 20 to about 175 μg/day and preferably from about 30 to about 150 μg/day of 17-p-estradiol. In other embodiments, the method of providing hormone replacement therapy is carried out by administering the compositions via a transdermal patch applied to the skin for seven days.

In another embodiment, compositions and methods as described in in copending application Ser. No. 10/879,710 titled "Process of Making Isomers of Norelgestromin and Methods Using the Same," filed Jun. 30, 2004, which is incoporated herein by reference in its entirety, can be likewise used with the high purity norelgestromin described herein, instead of the substantially pure norelgestromin oxime isomers described therein.

Definitions

The term "high purity," as used herein, means products/materials/compounds, in which the content of the specified compound is at least 99.5 mass percent and the overall of other steroid impurities is not more than 0.1 mass percent. For example, high purity norelgestromin contains at least 99.5 mass percent norelgestromin and contains not more than 0.1 mass percent other steroids.

The invention is illustrated by the following not limiting examples.

EXAMPLES

Example 1 d-(17α)-13-Ethyl-17-(acetyloxy)-18,19-dinorpegn-4-ene-20-yn-3-one (d-Norgestrel acetate)

Under nitrogen, to a vigorously stirred suspension of 150 g (about 0.45 mol) of d-norgestrel (purity 94%) and 1500 mL of acetic acid 135 mL (1.428 mol) of acetic anhydride and 3 mL of 70% aqueous perchloric acid are added. The suspension becomes clear in a few minutes. Stirring is continued for 20 mm, then 135 mL of water and 75 mL of 10% aqueous hydrochloric acid is added to the reaction mixture. After stirring for another 1 h, the reaction mixture is poured into 14 L of ice-water. The precipitated product is filtered off, washed with water, and dried. The obtained crude product is dissolved in 1500 mL of dichloromethane and stirred with 150 g of silica gel for 30 min for purification. The silica gel is filtered off, and the solvent is evaporated. The residue is refluxed with a 9:1 mixture of isopropyl ether/acetonitrile for 15 minutes. Then the solution is cooled to 0° C. The precipitated product is filtered off and dried to yield 137 g of the pure title compound. A further 19 g of the title compound can be obtained from the mother liquor by repeating the above purification process. Overall yield: 152 g (89.3%). Mp.: 204-205° C. $[\alpha]_D=-25°$ (c=1% in chloroform).

According to thin layer chromatography, the product contains less than 1% of impurity (calculated for d-norgestrel acetate). (For TLC DC-Alufolien Kieselgel 60 F254 plates and a 4:1 mixture of toluene-acetone, as eluent were used. Detection was carried out with a mixture of ethanol-sulfuric acid.)

Example 2 d-(17α)-13-Ethyl-17-(acetyloxy)-18,19-dinorpregna-4-ene-20-yn-3-one (d-Norgestrel acetate)

Under nitrogen, to a stirred suspension of 10 g (about 0.03 mol) of d-norgestrel (purity 93%) and 100 mL of acetic acid, 6 mL (0.063 mol) of acetic anhydride, 2 g of anhydrous zinc chloride, and 1.6 mL of 6.7% hydrogen chloride solution in acetic acid are added. The suspension becomes clear in a few minutes. Stirring is continued for 20 minutes, then 5 mL of water and after a further 15 minutes of stirring, 3 mL of 18% aqueous hydrochloric acid are added to the reaction mixture, which is stirred for a further 45 minutes. Then the reaction mixture is poured into 600 mL of ice-water. The precipitated product is filtered off, washed with water, and dried. The crude title compound is purified as described in Example 1.

Yield: 15.4 g (90.47%). Mp.: 204-205° C. $[\alpha]_D$=−25° (c=1% chloroform). Maximum impurity is 1% according to the analysis described in Example 1.

Example 3 d-(17α)-13-Ethyl-17-(acetyloxy)-18,19-dinorpregn-4-ene-20-yn-3-one-oxime (Norgestimate)

Under nitrogen, to a stirred solution of 12 g (0.033 mol) of d-norgestrel acetate, obtained according to methods described in Example 1 or 2, and 120 mL of acetic acid 9.44 g (0.1 mol) of hydroxylammonium acetate is added. The reaction mixture is stirred at room temperature for 45 minutes. Then it is poured into 1 L of water. The precipitated crystals are filtered off, washed with water until neutral, and dried below 40° C. in vacuum. The obtained 12.2 g of crude product is dissolved in 250 mL of boiling ethanol, stirred with 1.2 g of charcoal. After filtration of the charcoal, the solution is concentrated to a volume of about 20% of the original volume. The obtained solution containing the crystalline product is cooled to 0° C. and kept at this temperature for 12 h. The precipitated crystals are filtered off, washed with ethanol, and dried below 40° C. to yield 11.0 g (88%) of the title compound. Mp.: 224-226° C.

According to Test 1 and Test 2 described in USP 26th Pharmacopoeia on page 1335, the impurity of the product is less than 0.5%.

Example 4 d-(17α)-13-Ethyl-17-(acetyloxy)-18,19-dinorpregn-4-ene-20-yn-3-one-oxime (Norgestimate)

Under nitrogen, to a vigorously stirred solution of 120 g (0.33 mol) of d-norgestrel acetate, obtained according to the methods described in Examples 1 or 2, and 1259 g (1200 mL) of acetic acid 90.2 g (1.1 mol) of anhydrous sodium acetate and 76 g (1.93 mol) of hydroxylammonium hydrochloride are added. The temperature of the reaction mixture is preferably kept below 30° C. The reaction is completed in 1 hour. Then the obtained white suspension is poured into 10 L of water, and the obtained mixture is stirred for 30 mm. The precipitated product is filtered off, washed with water, and dried at 40° C.

The obtained crude product (122 g) is dissolved in 197.3 g (2500 mL) of boiling ethanol, decolorized with 12 g of charcoal and filtered. The filtrate is concentrated under reduced pressure below 40° C. to a volume of 400 mL. The filtrate is then cooled to 0-5° C. and kept at this temperature for 3 h. The precipitated white crystalline product is filtered off, washed with 197 g (250 mL) of ethanol in two portions, and dried below 40° C. to yield 102 g (81.6%) of the title compound. Mp.: 224-226° C.

According to Test 1 and Test 2 described in USP 26th Pharmacopoeia on page 1335, the impurity of the product is less than 0.5%.

Example 5 d-(17α)-13-Ethyl-17-hydroxy-18,19-dinorpregn-4-ene-20-yn-3-one-oxime (Norelgestrorin)

Under nitrogen, to a stirred suspension of 50.0 g (135.3 mmol) of norgestimate, obtained according to the procedures as described in Example 3 or 4, and 500 mL of methanol, 17.04 g (0.406 mol) of lithium hydroxide monohydrate is added at 20-28° C. After stirring for about 30 min, a homogeneous solution is obtained, and the temperature rises 10° C. The reaction mixture is stirred at 25-35° C. for 3 h or until the reaction is complete. Then the reaction mixture is poured into 5 L of water at 10-25° C. (the pH of the suspension is about 13). The pH of the suspension is adjusted to 7.5-9 with 14.7 mL (0.25 mol) of acetic acid. The obtained suspension is stirred for 20 minutes. Then the crystalline product is filtered off and washed twice with 200 mL of water. The pH of the filtrate is checked and washing is repeated until the pH of the filtrate is 7-7.5. The filtered crude product is dried at 50° C. The obtained 45 g of crude product is dissolved in 440 mL of ethanol at 25-30° C. Then 2.2 g of charcoal is added. After 20 min of stirring, the charcoal is filtered off and washed with ethanol. Then the filtrate is poured into 4.4 L of water at 10-25° C. under vigorous stirring. The obtained product is filtered off, washed with water, and dried at 50° C. to yield 42.0 g (94.8%) of the title compound. Mp.: 110-130° C. Water content is 0.4%.

The purity of the obtained norelgestromin samples was determined by HPLC using a Shimadzu instrument, UV detection and Shimadzu integrator. Detection was performed at 244 nm. A 150×4.6 mm column, filled with 5 vim size Supelcosil LC-18-DB packing material, was used. A 7:25:68 mixture of acetonitrile:tetrahydrofuran:water was used as eluent. The determination was carried out at room temperature, with a flow rate of 1 cm³/min.

The sample solution was prepared as follows: 25 mg of the compound was measured into a 50 mL volumetric flask, 5 mL of methanol was added, and the sample was dissolved. Then the flask was filled with the eluent to the calibration line. The standard solution (STD) was prepared the same way from analytical pure norelgestromin, containing the E/Z isomers in a ratio between 1.3-1.6.

The amount of impurity in % (S %) was calculated by the following formula:

In the formula:

| | |
|---|---|
| A = | area under the curve for the component in the subscript |
| $C_{STD}$ = | concentration of the standard solution (mg/mL) |
| $A_{STD\ calc.}$ = | $A_{STD,E}$ × 0.72 + $A_{STD,Z}$ (subscript E means the data of E isomer, subscript Z means that of the Z isomer) |
| $C_{sample}$ = | concentration of the sample solution (mg/mL) |

The response factors (rf) of the known components are as follows:

| | |
|---|---|
| d-norgestrel = | 0.78 |
| norelgestromin Z isomer = | 1.00 |
| norelgestromin E isomer = | 0.72 |

-continued

| | |
|---|---|
| norgestimate Z isomer = | 1.08 |
| norgestimate E isomer = | 0.81 |
| in the case of unknown impurity = | 1.00 |

The result of the above HPLC determination is altogether 0.1% of impurities. NMR measurements:

$^1$H NMR (500 M)Hz, DMSO-d$_6$(TMS), δ (ppm) Z/E isomer): 0.92/0.92 (3H, t, —CH$_2$—CH$_3$), 1.40/1.40 (2H, m, —CH$_2$—CH$_3$), 2.05 & 2.24/1.87 & 2.87 (2H, m, H-2), 3.28/3.28 (1H, s, ≡CH), 5.23/5.23 (1H, s, 17-OH), 6.40/5.78 (1H, m, H-4), 10.12/10.38 (1H, s, =N—OH).

$^{13}$C NMR (125 MHz. DMSO-d$_6$ (TMS 0.8 ppm Z/E isomer): 9.4/9.4 (—CH—CH$_3$), 18.3/18.3 (—CH$_2$—CH$_3$), 26.9/20.6 (C-2), 79.6/79.6 (C-17), 89.1/89.1 (—C≡), 74.9/74.9 (≡CH), 111.6/118.6 (C-4), 151.2/154.3 (C-3), 152.0/148.1 (C-5).

Example 6 d-(17α)-13-Ethyl-17-hydroxy-18,19-dinorpregn-4-ene-20-yn-3-one-oxime (Norelgestromin)

Under nitrogen, to a stirred suspension of 10.0 g (0.027 mol) of norgestimate (d-norgestrel-acetate-oxime), obtained according to the method described in Example 3 or 4, and 100 mL of methanol 3.25 g (0.081 mol) of sodium hydroxide is added at 22° C. After stirring for about 10 min, a homogeneous solution is obtained, and the temperature rises to 32° C. Then the reaction mixture is stirred at 25° C. for another 3 h until the reaction is complete. The reaction mixture is poured into 1000 mL of water at 10-20° C. under stirring, and the pH of the suspension is adjusted to 7-7.5 with 3 mL of acetic acid. Then the obtained suspension is stirred for another 20 min. The precipitated product is filtered off, washed with water, and dried under vacuum at 40° C. over phosphorous pentoxide to yield 8.4 g (94.8%) of the title compound as a mixture of 3E and 3Z isomers. Mp.: 110-130° C. According to HPLC, the amount of all the impurities is 0.09%.

Example 7 d-(17α)-13-Ethyl-17-hydroxy-18,19-dinorpregn-4-ene-20-yn-3-one-oxime (Norelgestromin)

Under nitrogen, to a stirred suspension of 10.0 g (0.027 mol) of norgestimate (d-norgestrel-acetate-oxime), obtained according to Example 3 or 4, and 100 mL of methanol 4.56 g (0.081 mol) of potassium hydroxide is added at 22° C. After stirring for about 10 min, a homogeneous solution is obtained, and the temperature rises to 32° C. Then the reaction mixture is stirred at 25° C. for another 3 h until the reaction is complete. The reaction mixture is poured into 1000 mL of water at 10-20° C. under stirring, and the pH of the suspension is adjusted to 7-7.5 with 2.7 mL of acetic acid. The suspension obtained is stirred for 20 min. The precipitated product is filtered off, washed with water until neutral, and dried under vacuum at 40° C. over phosphorous pentoxide to yield 8.6 g (96.9%) of the title compound as a mixture of 3E and 3Z oxime isomers. Mp.: 110-130° C. According to HPLC the amount of all the impurities is 0.1%.

Having now fully described this invention, it will be understood by those of ordinary skill in the art that the same can be performed within a wide and equivalent range of conditions, formulations and other parameters without affecting the scope of the invention or any embodiment thereof. All patents and publications cited herein are fully incorporated by reference herein in their entirety.

What is claimed is:

1. A process for the synthesis of high purity d-(17α)-13-ethyl-17-hydroxy-18,19-dinorpregn-4-ene-20-yne-3-one-oxime via acetylation of d-norgestrel at position 17, oximation of the oxo group at position 3 of the obtained 17-acetoxy derivative, and hydrolyzing the acetoxy group at position 17 of the obtained 3-oxime derivative, characterized by:

carrying out the acetylation of d-(17α)-17-hydroxy-13-ethyl-18,19-dinorpregn-4-ene-20-yne-3-one (d-norgestrel), having a purity of at least 93%, with acetic anhydride in acetic acid, in the presence of zinc chloride and hydrogen chloride, or 70% perchloric acid in an inert gas atmosphere, and after completion of the reaction decomposing any excess of acetic anhydride and any enol acetate by-product with aqueous hydrochloric acid;

isolating the formed d-(17α)-17-acetoxy-13-ethyl-18,19-dinorpregn-4-ene-20-yne-3-one from the reaction mixture by addition of ice-water, filtering off the precipitated product, washing the precipitated product with water, drying the precipitated product, dissolving the precipitated product in dichloromethane or acetone and clarifying with silica gel or aluminum oxide and charcoal, concentrating the resulted solution after filtration of the clarifier and recrystallizing the residue;

reacting the obtained d-(17α)-17-acetoxy-13ethyl-18,19-dinorpregn-4-ene-20-yne-3-one either with hydroxyl ammonium acetate or with hydroxyl ammonium chloride in the presence of sodium acetate, in acetic acid in nitrogen atmosphere under vigorous stirring for about 1 hour, addition of water after completion of the reaction, filtering off the precipitated product, washing with water, drying and recrystallizing; and hydrolyzing the obtained d-(17α)-17-acetoxy-13-ethyl-18,19-dinorpregn-4-ene-20-yne-3-one-oxime with an equivalent amount of an alkali metal hydroxide in a C$_1$-C$_4$ alkanol solution, in nitrogen atmosphere between a temperature of about 5° C. to about 38° C., under vigorous stirring, diluting the reaction mixture with water after completion of the reaction and adjusting the pH of the resulted suspension to 7.5-9 with acetic acid, filtering off the precipitated product, washing with water, drying, dissolving the crude product in ethanol, clarifying with charcoal, and addition of water after filtration of the clarifier to the obtained solution, filtering off the precipitated high purity d-(17α)-17-hydroxy-13-ethyl-18,19-dinorpregn-4-ene-20-yne-3-one-oxime, washing with water and optionally recrystallizing from ethanol.

2. The process according to claim 1, characterized by hydrolyzing the d-(17α)-17-acetoxy-13-ethyl-18,19-dinorpregn-4-ene-20-yne-3-one-oxime in methanol with lithium hydroxide monohydrate.

3. The process according to claim 1, characterized by recrystallizing the obtained d-(17α)-17-acetoxy-13-ethyl-18,19-dinorpregn-4-ene-20-yne-3-one from a 9:1 mixture of diisopropyl ether/acetonitrile or diisopropyl ether/ethanol.

4. The process according to claim 1, characterized by recrystallizing the obtained d-(17α)-17-acetoxy-13-ethyl-18,19-dinorpregn-4-ene-20-yne-3-one-oxime from ethanol.

5. A process for the synthesis of high purity d-(17α)-13-ethyl-17-hydroxy-18,19-dinorpregn-4-ene-20-yne-3-one-oxime via acetylation of d-norgestrel at position 17, oximation of the oxo group at position 3 of the obtained 17-acetoxy derivative, and hydrolyzing the acetoxy group at position 17 of the obtained 3-oxime derivative, wherein the d-(17α)-13-ethyl-17-hydroxy-18,19-dinorpregn-4-ene-20-yne-3-one-oxime product has a purity of 99.5% or greater and is provided in an overall yield of 68% or greater, and wherein the process is characterized by:

carrying out the acetylation of d-(17α)-17-hydroxy-13-ethyl-18,19-dinorpregn-4-ene-20-yne-3-one (d-norgestrel), having a purity of at least 93%, with acetic anhydride in acetic acid, in the presence of zinc chloride and hydrogen chloride, or 70% perchloric acid in an inert gas atmosphere, and after completion of the reaction decomposing any excess of acetic anhydride and any enol acetate by-product with aqueous hydrochloric acid;

isolating the formed d-(17α)-17-acetoxy-13-ethyl-18,19-dinorpregn-4-ene-20-yne-3-one from the reaction mixture by addition of ice-water, filtering off the precipitated product, washing the precipitated product with water, drying the precipitated product, dissolving the precipitated product in dichloromethane or acetone and clarifying with silica gel or aluminum oxide and charcoal, concentrating the resulted solution after filtration of the clarifier and recrystallizing the residue;

reacting the obtained d-(17α)-17-acetoxy-13-ethyl-18,19-dinorpregn-4-ene-20-yne-3-one either with hydroxyl ammonium acetate or with hydroxyl ammonium chloride in the presence of sodium acetate, in acetic acid in nitrogen atmosphere under vigorous stirring for about 1 hour, addition of water after completion of the reaction, filtering off the precipitated product, washing with water, drying and recrystallizing; and hydrolyzing the obtained d-(17α)-17-acetoxy-13-ethyl-18,19-dinorpregn-4-ene-20-yne-3-one-oxime with an equivalent amount of an alkali metal hydroxide in a $C_1$-$C_4$ alkanol solution, in nitrogen atmosphere between a temperature of about 5° C. to about 38° C., under vigorous stirring, diluting the reaction mixture with water after completion of the reaction and adjusting the pH of the resulted suspension to 7.5-9 with acetic acid, filtering off the precipitated product, washing with water, drying, dissolving the crude product in ethanol, clarifying with charcoal, and addition of water after filtration of the clarifier to the obtained solution, filtering off the precipitated high purity d-(17α)-17-hydroxy-13-ethyl-18,19-dinorpregn-4-ene-20-yne-3-one-oxime, washing with water and optionally recrystallizing from ethanol.

6. The process according to claim 5, wherein the d-(17α)-13-ethyl-17-hydroxy-18,19-dinorpregn-4-ene-20-yne-3-one-oxime product has a purity of 99.9% or greater.

7. The process according to claim 5, wherein the d-norgestrel starting material is present in an amount of at least 150 g.

8. The process according to claim 5, wherein the d-norgestrel starting material is present in an amount of at least 150 g and has a purity of 93% to about 94%.

9. The process according to claim 5, characterized by hydrolyzing the d-(17α)-17-acetoxy-13-ethyl-18,19-dinorpregn-4-ene-20-yne-3-one-oxime in methanol with lithium hydroxide monohydrate.

10. The process according to claim 5, characterized by recrystallizing the obtained d-(17α)-17-acetoxy-13-ethyl-18,19-dinorpregn-4-ene-20-yne-3-one from a 9:1 mixture of diisopropyl ether/acetonitrile or diisopropyl ether/ethanol.

11. The process according to claim 5, characterized by recrystallizing the obtained d-(17α)-17-acetoxy-13-ethyl-18,19-dinorpregn-4-ene-20-yne-3-one-oxime from ethanol.

12. The process according to claim 5, wherein the acetylation of d-norgestrel provides d-(17α)-17-acetoxy-13-ethyl-18,19-dinorpregn-4-ene-20-yne-3-one in a yield of 89% or greater.

13. The process according to claim 5, wherein the oximation of d-(17α)-17-acetoxy-13-ethyl-18,19-dinorpregn-4-ene-20-yne-3-one provides d-(17α)-17-acetoxy-13-ethyl-18,19-dinorpregn-4-ene-20-yne-3-one-oxime in a yield of 81% or greater.

14. The process according to claim 5, wherein the hydrolyzing d-(17α)-17-acetoxy-13-ethyl-18,19-dinorpregn-4-ene-20-yne-3-one-oxime provides d-(17α)-17-hydroxy-13-ethyl-18,19-dinorpregn-4-ene-20-yne-3-one-oxime in a yield of 95% or greater.

* * * * *